(12) United States Patent
Bastian

(10) Patent No.: US 7,888,039 B2
(45) Date of Patent: Feb. 15, 2011

(54) ASSAY FOR TRANSMISSIBLE SPONGIFORM ENCEPHALOPATHIES

(75) Inventor: Frank O. Bastian, New Orleans, LA (US)

(73) Assignees: Board of Supervisors of Louisiana State University and Agricultural and Mechanical College, Baton Rouge, LA (US); The Administrators of the Tulane Educational Fund, New Orleans, LA (US)

( * ) Notice: Subject to any disclaimer, the term of this patent is extended or adjusted under 35 U.S.C. 154(b) by 901 days.

(21) Appl. No.: 11/597,068

(22) PCT Filed: May 23, 2005

(86) PCT No.: PCT/US2005/017904

§ 371 (c)(1),
(2), (4) Date: Nov. 20, 2006

(87) PCT Pub. No.: WO2005/115483

PCT Pub. Date: Dec. 8, 2005

(65) Prior Publication Data

US 2009/0291460 A1    Nov. 26, 2009

Related U.S. Application Data

(60) Provisional application No. 60/573,814, filed on May 24, 2004.

(51) Int. Cl.
G01N 33/53 (2006.01)
A61K 39/00 (2006.01)
C07H 21/04 (2006.01)

(52) U.S. Cl. .............................. 435/7.1; 435/4; 435/7.2; 530/300; 530/350; 536/23.1; 536/23.7; 424/130.1; 424/139.1; 424/164.1; 424/184.1; 424/185.1; 424/190.1

(58) Field of Classification Search .............. 424/130.1, 424/139.1, 164.1, 184.1, 185.1, 190.1; 435/4, 435/7.1, 7.2; 530/300, 350; 536/23.1, 23.7
See application file for complete search history.

(56) References Cited

U.S. PATENT DOCUMENTS

| | | | |
|---|---|---|---|
| 6,033,858 A | 3/2000 | Bastian | 435/6 |
| 2004/0175775 A1 | 9/2004 | Cashman | 33/53 |

OTHER PUBLICATIONS

Bastian, Frank.O. et al., "Antiserum to Scrapie-Associated Fibril Protein Cross-Reacts with *Spiroplasma mirum* Fibral Proteins," J. of Clin. Microbiology, vol. 25, No. 12, pp. 2430-2431 (1987).

Bastian, F. et al., "Linking chronic wasting disease to scrapie by comparison of *Spiroplasma mirum* ribosomal DNA sequences," *Exper. Molec. Pathol.*, vol. 77, pp. 49-56 (2004).
Butler, G.H. et al., "Identification and Characterization of Proteinase K-resistant Proteins in Members of the Class Mollicutes," Infection and Immunity, vol. 59, No. 3, pp. 1037-1042 (1991).
Friedlaender, R. et al., "Ocular pathology induced by the suckling mouse cataract agent," *Investigative Ophthalmology*, vol. 15, pp. 640-647 (1976).
Kirchhoff, H. et al., "Pathogenicity of *Spiroplasma* sp. strain SMCA in rabbits: clinical, microbiological, and histological aspects," *Infection & Immunity*, vol. 33(1), pp. 292-296 (1981).
Kirchhoff, H. et al., "Pathogenicity of *Spiroplasma* sp. strain SMCA in Syrian hamsters: clinical, microbiological, and histological aspects," *Infection & Immunity*, vol. 31(1), pp. 445-452 (1981).
Lorenz, B. et al., "First evidence of an endogenous *Spiroplasma* sp. infection in humans manifesting as unilateral cataract associated with anterior uveitis in a premature baby," *Graefe's Arch. Clin. Exp. Ophthalmol.*, vol. 240 (5), pp. 348-353 (2002).
Olmsted, E. et al., "Ocular lesions induced in C57 mice by the suckling mouse cataract agent (SMCA)," *Investigative Ophthalmology and Visual Science*, vol. 5, pp. 413-420 (1966).
Sakaguchi, S. et al., "Kinetics of infectivity are dissociated from PrP accumulation in salivary glands of Creutzfeldt-Jakob disease agent-inoculated mice," *J. Gen. Virol.*, vol. 74, pp. 2117-2123 (1993).
Tully, Joseph G. et al., "Pathogenic Mycoplasmas: Cultivation and Vertebrate Pathogenicity of a New *Spiroplasma*," Science, vol. 195, pp. 892-894 (1977).
Wadsworth, J. et al., "Tissue distribution of protease resistant prior protein in variant Creutzfeldt-Jakob disease using a highly sensitive immunoblotting assay," *The Lancet*, vol. 358, pp. 171-180.(2001).
Zeigel, R. et al., "Electron microscopy of the suckling mouse cataract agent: a noncultivatable animal pathogen possibly related to Mycoplasma," *Infection and Immunity*, vol. 9, pp. 430-443 (1974).

*Primary Examiner*—Rodney P. Swartz
(74) *Attorney, Agent, or Firm*—John H. Runnels; Bonnie J. Davis

(57) ABSTRACT

Provided is a novel method for detecting Transmissible Spongiform encephalopathies (TSE). The method comprises: selecting a body fluid sample from a subject to determine whether the subject has transmissible spongiform encephalopathy; and detecting antibodies that immune react with *Spiroplasma* proteins in the sample. The method detects antibodies in the individual sera samples that react with recombinant *Spiroplasma*-specific Hsp60 by standard ELISA methodology. This method provides for rapid detection of TSE by determination of presence of antibodies in test samples showing associated Spiroplasma infection that has become consistent with presence of TSE. The method provides a mechanism to detect presence of TSE without invasive techniques currently needed to make diagnosis using brain tissues for prion detection. This method provides means of detection of TSE in the live patient without need for using necropsy tissues. This method provides the first method discovered that detects antibodies against TSE infection-specific proteins in serum or cerebrospinal fluid or other body fluid samples.

31 Claims, 4 Drawing Sheets

```
                              SEQUENCE LISTING

<160> NUMBER OF SEQ ID NOS: 2

<210> SEQ ID NO 1
<211> LENGTH: 984
<212> TYPE: DNA
<213> ORGANISM: Spiroplasma mirum
<220> FEATURE:
<221> NAME/KEY: CDS
<222> LOCATION: (2) ... (982), (888)
<223> OTHER INFORMATION: Expressed protein, n is an unknown nucleotide

<400> SEQUENCE: 1 t gat att gct ggg gac ggt act acc act gca att gtt tta act cag gca         49
  Asp Ile Ala Gly Asp Gly Thr Thr Thr Ala Ile Val Leu Thr Gln Ala
   1               5                  10                  15 att gtt aaa gag gga tta aaa aat att acc gct ggt gca aat gct gta           97
Ile Val Lys Glu Gly Leu Lys Asn Ile Thr Ala Gly Ala Asn Ala Val
                20                  25                  30 gct att cgt aat gga att gaa aaa aca gtt aaa gcg att gtg gat tta          145
Ala Ile Arg Asn Gly Ile Glu Lys Thr Val Lys Ala Ile Val Asp Leu
            35                  40                  45 cta aaa caa tca gca aag gaa att aag tca aaa gaa gaa att gca caa          193
Leu Lys Gln Ser Ala Lys Glu Ile Lys Ser Lys Glu Glu Ile Ala Gln
 50                  55                  60 gtt gca agt gtc agt tca aaa gac ctt gaa att ggt gct tta att gct          241
Val Ala Ser Val Ser Ser Lys Asp Leu Glu Ile Gly Ala Leu Ile Ala
 65                  70                  75                  80 gaa att atg gcc aaa gtt ggt aat gat ggt gtt att acg att gaa gaa          289
Glu Ile Met Ala Lys Val Gly Asn Asp Gly Val Ile Thr Ile Glu Glu
                85                  90                  95 tca aaa aca att aat act gaa aca agt gtt act gaa gga tta caa ttt          337
Ser Lys Thr Ile Asn Thr Glu Thr Ser Val Thr Glu Gly Leu Gln Phe
            100                 105                 110 gat aaa gga tat tta tca caa tac atg gtc act gat agt gaa aaa atg          385
Asp Lys Gly Tyr Leu Ser Gln Tyr Met Val Thr Asp Ser Glu Lys Met
        115                 120                 125 tta aca gaa ttt gaa aat cca tat att tta att acg gat aaa aaa att          433
Leu Thr Glu Phe Glu Asn Pro Tyr Ile Leu Ile Thr Asp Lys Lys Ile
    130                 135                 140 agt aat atg aaa gaa att cta cca att tta gaa aaa att gtt gaa gaa          481
Ser Asn Met Lys Glu Ile Leu Pro Ile Leu Glu Lys Ile Val Glu Glu
145                 150                 155                 160 gga cgt cca tta tta att att gct gat gat gtt gat ggt gat gtt tta          529
Gly Arg Pro Leu Leu Ile Ile Ala Asp Asp Val Asp Gly Asp Val Leu
                165                 170                 175 cca aca tta tta ttg aac aaa atg cgt ggt gct ttt aat att tgt gtt          577
Pro Thr Leu Leu Leu Asn Lys Met Arg Gly Ala Phe Asn Ile Cys Val
            180                 185                 190 gtt aaa gcg ccc gaa ttt gga aac aac cgt aag gat tta tta gaa gat          625
Val Lys Ala Pro Glu Phe Gly Asn Asn Arg Lys Asp Leu Leu Glu Asp
        195                 200                 205
```

-continued

```
att gct atg cta gta aaa ggt aaa ttt gtt aat ggt gat tta gga atg      673
Ile Ala Met Leu Val Lys Gly Lys Phe Val Asn Gly Asp Leu Gly Met
210                 215                 220 gat tta aaa acc tta aca tta gat gat tta gga act gca aaa aaa gta      721
Asp Leu Lys Thr Leu Thr Leu Asp Asp Leu Gly Thr Ala Lys Lys Val
225                 230                 235                 240 att gtt tca aaa gat aca aca aca att att gaa gga aaa gcg aca cgt      769
Ile Val Ser Lys Asp Thr Thr Thr Ile Ile Glu Gly Lys Ala Thr Arg
                245                 250                 255 gca gaa att gaa gct cgc aaa gat ttt att cgt cat caa att gaa aat      817
Ala Glu Ile Glu Ala Arg Lys Asp Phe Ile Arg His Gln Ile Glu Asn
            260                 265                 270 gaa aaa tca aca ttt gaa caa gat aaa ttg aaa aaa aga tta gct aaa      865
Glu Lys Ser Thr Phe Glu Gln Asp Lys Leu Lys Lys Arg Leu Ala Lys
        275                 280                 285 ctt gct aat ggt gtt gga att ant aaa gtt ggt gca cca act gaa aca      913
Leu Ala Asn Gly Val Gly Ile Xaa Lys Val Gly Ala Pro Thr Glu Thr
    290                 295                 300 gaa atg aaa gag aag aaa tta cga att gaa gat gcc tta aac tcg act      961
Glu Met Lys Glu Lys Lys Leu Arg Ile Glu Asp Ala Leu Asn Ser Thr
305                 310                 315                 320 aag gca gct gtt gaa gaa gtg at                                       984
Lys Ala Ala Val Glu Glu Val
                325
```

<210> SEQ ID NO 2
<211> LENGTH: 327
<212> TYPE: PRT
<213> ORGANISM: Spiroplasma mirum
<220> FEATURE:
<221> NAME/KEY: misc_feature
<222> LOCATION: 296
<223> OTHER INFORMATION: Xaa is an unknown amino acid

<400> SEQUENCE: 2

```
Asp Ile Ala Gly Asp Gly Thr Thr Thr Ala Ile Val Leu Thr Gln Ala
  1               5                  10                  15

Ile Val Lys Glu Gly Leu Lys Asn Ile Thr Ala Gly Ala Asn Ala Val
                 20                  25                  30

Ala Ile Arg Asn Gly Ile Glu Lys Thr Val Lys Ala Ile Val Asp Leu
             35                  40                  45

Leu Lys Gln Ser Ala Lys Glu Ile Lys Ser Lys Glu Glu Ile Ala Gln
 50                  55                  60

Val Ala Ser Val Ser Ser Lys Asp Leu Glu Ile Gly Ala Leu Ile Ala
 65                  70                  75                  80

Glu Ile Met Ala Lys Val Gly Asn Asp Gly Val Ile Thr Ile Glu Glu
                 85                  90                  95

Ser Lys Thr Ile Asn Thr Glu Thr Ser Val Thr Glu Gly Leu Gln Phe
            100                 105                 110

Asp Lys Gly Tyr Leu Ser Gln Tyr Met Val Thr Asp Ser Glu Lys Met
        115                 120                 125

Leu Thr Glu Phe Glu Asn Pro Tyr Ile Leu Ile Thr Asp Lys Lys Ile
130                 135                 140

Ser Asn Met Lys Glu Ile Leu Pro Ile Leu Glu Lys Ile Val Glu Glu
145                 150                 155                 160

Gly Arg Pro Leu Leu Ile Ile Ala Asp Asp Val Asp Gly Asp Val Leu
                165                 170                 175

Pro Thr Leu Leu Leu Asn Lys Met Arg Gly Ala Phe Asn Ile Cys Val
```

-continued

```
              180                 185                 190
Val Lys Ala Pro Glu Phe Gly Asn Asn Arg Lys Asp Leu Leu Glu Asp
        195                 200                 205

Ile Ala Met Leu Val Lys Gly Lys Phe Val Asn Gly Asp Leu Gly Met
        210                 215                 220

Asp Leu Lys Thr Leu Thr Leu Asp Asp Leu Gly Thr Ala Lys Lys Val
225                     230                 235                 240

Ile Val Ser Lys Asp Thr Thr Thr Ile Ile Glu Gly Lys Ala Thr Arg
                245                 250                 255

Ala Glu Ile Glu Ala Arg Lys Asp Phe Ile Arg His Gln Ile Glu Asn
                260                 265                 270

Glu Lys Ser Thr Phe Glu Gln Asp Lys Leu Lys Lys Arg Leu Ala Lys
        275                 280                 285

Leu Ala Asn Gly Val Gly Ile Xaa Lys Val Gly Ala Pro Thr Glu Thr
        290                 295                 300

Glu Met Lys Glu Lys Lys Leu Arg Ile Glu Asp Ala Leu Asn Ser Thr
305                 310                 315                 320

Lys Ala Ala Val Glu Glu Val
                325
```

ASSAY FOR TRANSMISSIBLE SPONGIFORM ENCEPHALOPATHIES

This application claims priority from U.S. Provisional Application Ser. No. 60/573,814 ("the '814 application") filed May 24, 2004. The '814 application is incorporated herein by reference.

This work was supported by NIH NINDS 5RO1NS044000-O3 to Frank O. Bastian.

BACKGROUND OF THE INVENTION

The present invention presents an assay for transmissible spongiform encephalopathies in humans and other animals.

Transmissible spongiform encephalopathies ("TSE") are diseases that can affect humans and other animals. It is characterized by spongy degeneration of the brain. The disease is known as scrapie in sheep and goats. The condition is known as both bovine spongiform encephalopathy or mad cow disease in cattle. There exist human variants of the disease known as Kuru, Creutzfeldt-Jakob Disease ("CJD"), fatal familial insomnia, and Gerstmann-Strausler disease. Deer and elk are known to contract a variant of the disease known as chronic wasting disease. TSE is seen in farmed mink, known as transmissible mink encephalopathy.

At a molecular level, the disease is characterized by deposition of prion protein in brains from TSE-afflicted humans or animals. The prion protein is a normal constituent of brain tissue. In individuals affected by transmissible spongiform encephalopathies, there is conformational change in the protein making it resistant to denaturation by proteolytic enzymes. Since the prion proteins of affected individuals are resistant to most methods of denaturation, most assays for the diseased version of the protein seek to differentiate between the diseased and normal version of the protein. Typical assays for the protein first treat suspected brain tissue with proteolytic enzymes, then seek to identify the prion proteins (usually by polyacrylamide gel electrophoresis followed by western blotting with an antibody specific for both types of prion proteins). In unaffected individuals, there is often no protein available for recognition by the antibodies during western blotting following proteolytic digestion. Because of the ability of diseased prion proteins to resist proteolytic denaturation, they are recognized by the anti-prion antibodies. An alternate approach is to use antibody recognition of the prion protein by Enzyme-Linked ImmunoadSorbent Assay ("ELISA") using antibodies tagged with enzymes or fluorescent molecules. In either case, a fluorescent or calorimetric signal can be used to conclude the testing. Abnormal Prion has not been detected in sera or cerebrospinal fluid derived from TSE-afflicted individuals.

Current methods of testing for the presence of transmissible spongiform encephalopathies are for the most part conducted post-mortem. This is because an analysis of the prion proteins of the individuals must be done and this is accomplished, by an analysis of brain tissue or other tissues such as tonsil. Thus, such analyses are extremely invasive negating applicability to preclinical diagnosis of TSE. These assays, while useful, suffer from their reliance on brain tissue to provide a diagnostic result. The use of brain material is not feasible for screening. This is especially not suitable when the individual to be tested is a living human or for the purpose only to determine if the individual is a safe blood donor. Therefore there exists a need to develop a test that can provide diagnosis in a living individual with minimal invasion, preferably using sera samples.

An alternate approach has led to a better understanding of the pathogenesis of TSE whereby a wall-less bacterium called *Spiroplasma* is closely associated with these diseases. The presence of *Spiroplasma* was initially discovered in an ultrastructural study of a brain biopsy obtained from a 46 year old CJD patient. Since then, the presence of *Spiroplasma* genes in TSE brain tissues has been shown using molecular techniques including polymerase chain reaction (PCR), Southern blotting and DNA sequence analyses. More recently, a unique *Spiroplasma* species from TSE-infected brain tissues has been isolated by passage through embryonated eggs into cell-free media. The role of *Spiroplasma* infection in the pathogenesis of TSE is supported by recent studies that have shown the normal prion isoform to serve as a receptor protein for a bacterium. It is presumed that interaction of *Spiroplasma* with the prion results in the disease and accumulation of the misfolded prion protein.

The occurrence of a consistent *Spiroplasma* infection in association with individual TSE cases provided the opportunity to develop a serum test for the disease based upon the presence of antibodies generated against *Spiroplasma* proteins. Heat shock protein 60 (Hsp60) was chosen because of prior data that showed interaction of bacterial-specific Hsp60 protein on the bacterial surface with the prion receptor. It is noteworthy that Hsp60 is widespread in nature. However, the Hsp60 of bacteria is specific in that there is 70% homology with other bacteria, but a 100% homology among strains of the same genus. There is 50% homology of bacterial Hsp60 with human Hsp60 proteins. The inventor has isolated the Hsp60 gene specific for *Spiroplasma*, produced recombinant *Spiroplasma*-specific Hsp60 recombinant protein and shown reactivity with sera from individual TSE cases by using ELISA.

The current methods of testing are also inefficient when applied to large numbers of livestock. Brain or neural material must be taken after slaughter and processed to be assayed. This delay can result in the carcass of the animal being placed into the human or animal food supply before testing can be concluded. Also, these postmortem assays cannot be used to test and produce groups of animals that are free of transmissible spongiform encephalopathies or insure that animals with transmissible spongiform encephalopathy do not comingle with disease free animals. The use of brain tissue, in addition to mandating a postmortem test, is also very inconvenient. An assay using a more readily available bodily fluid such as sera or tissue offers a more convenient approach to testing of any animal type for TSE.

SUMMARY OF THE INVENTION

The present invention relates to methods of detecting transmissible spongiform encephalopathies in animals, including human beings. The invention relies on the use of a protein of the *Spiroplasma* bacterium to identify individuals affected with transmissible spongiform encephalopathies. Specifically, this invention uses the heat shock protein 60 (Hsp60) of *Spiroplasma mirum*. Alternatively, other proteins of *Spiroplasma mirum* could be used in place of Hsp60 in this assay. Additionally, the proteins of other members of the genus *Spiroplasma* could be used to create the assay. Artificially synthesized peptides representing amino acid fragments of proteins from the genus *Spiroplasma* may also be used.

The present invention uses the serum of an animal or human being as its testing material. In another embodiment of the invention, whole blood may be used as the testing material. In yet another embodiment of the present invention, cerebrospinal fluid of an animal or human being may serve as the testing material. Other body fluids such as urine, tears and saliva may also serve as a testing material.

It is an object of the invention to provide a method of detecting a transmissible spongiform encephalopathy (TSE) disease in a mammal, including a human, a cow and a sheep, comprising detecting the presence of an antibody to a protein from a bacterium of the genus *Spiroplasma* in the serum of the mammal.

It is an object of this invention to provide a method of detecting a transmissible spongiform encephalopathy (TSE) disease in a mammal, including a human, a cow and a sheep, comprising contacting a serum sample from a mammal with at least a portion of heat shock protein 60 (Hsp60) from a *Spiroplasma* bacterium and detecting a reaction product of Hsp60 or a portion thereof with a component of the plasma.

It is a further object of this invention to provide a method of diagnosing a TSE disease in a mammal comprising detecting the presence of a *Spiroplasma* infection in a mammal.

It is a further object of this invention to provide a method of diagnosing a TSE disease in a mammal comprising detecting an antibody to *Spiroplasma* Hsp60 in a serum sample from a mammal.

It is a further object of this invention to provide a method of diagnosing a TSE disease in a mammal comprising detecting an antibody to *Spiroplasma* Hsp60 in a cerebrospinal fluid sample from a mammal.

It is a further object of this invention to provide a method of diagnosing a TSE disease in a mammal comprising detecting an antibody to *Spiroplasma* Hsp60 in a whole blood sample from a mammal.

It is a further object of this invention to provide an isolated Hsp60 protein and an isolated polynucleotide encoding an Hsp60 protein having DNA and amino acid sequences of SEQ ID NO. 1, and SEQ ID NO. 2, respectively.

DETAILED DESCRIPTION OF THE INVENTION

Figure 1:
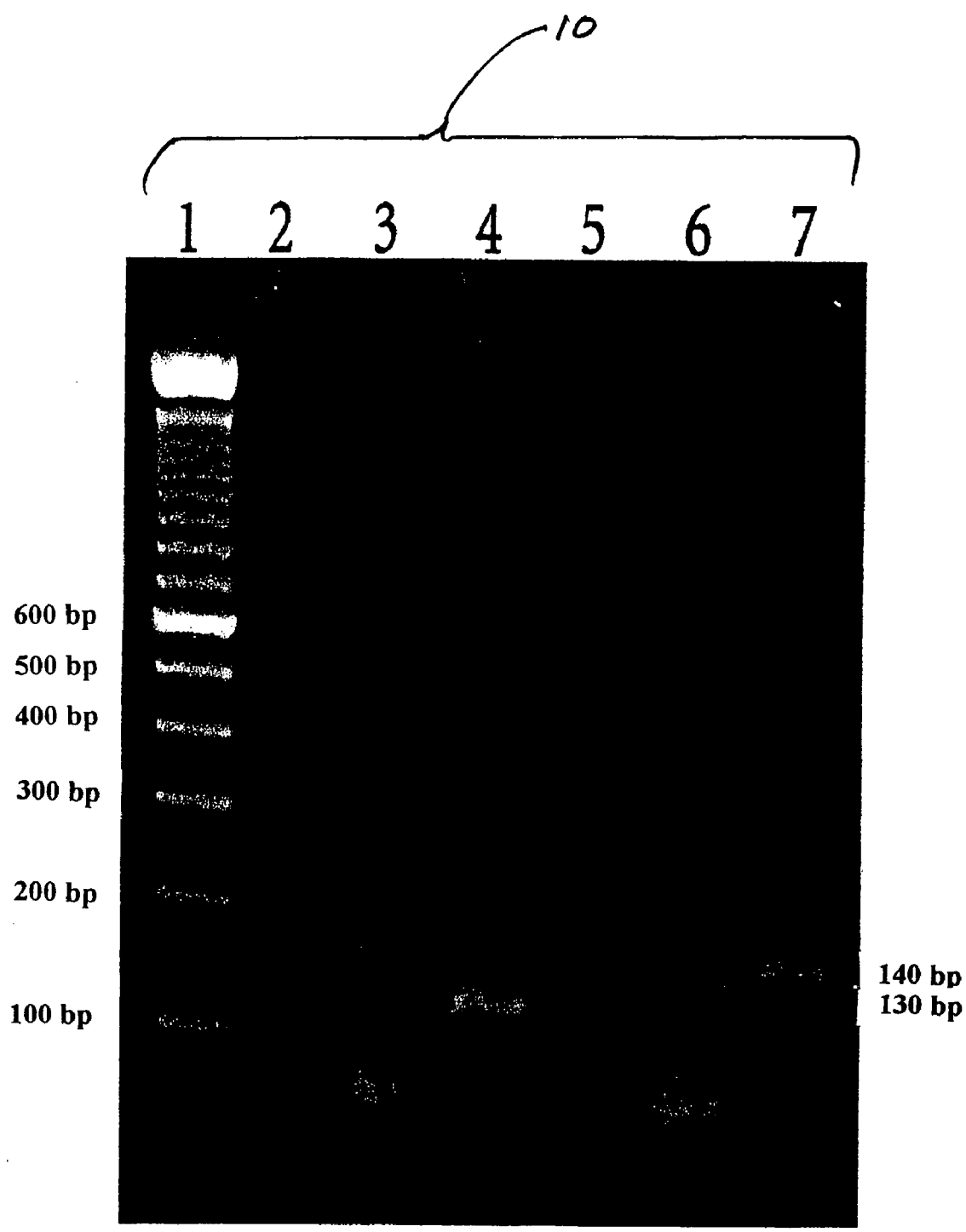
FIG. 1 is an illustrative gel electrophoresis of polymerase chain reaction (PCR) generated amplified products obtained by probing TSE and normal brain tissues using oligonucleotide primers specific for *Spiroplasma* Hsp60 gene. The PCR amplified *Spiroplasma* Hsp60 gene product is only present in the TSE infected brain but not in normal brain or water control.

The gene for heat shock protein 60 (Hsp60) of *Spiroplasma mirum* (GenBank ID M24662) was identified by polymerase chain reaction (PCR) and DNA sequence analysis. The gene was cloned in a Topo vector (Invitrogen). The DNA and predicted amino acid sequence of *Spiroplasma mirum* Hsp60 is not in the GenBank, has not been published, and is claimed here as part of this invention as described in SEQ ID NO 1 and SEQ ID NO 2. New oligonucleotide primers were designed from this novel sequence and used to probe DNA extracts from TSE brain tissues. As depicted in FIG. 1, which has a series of lanes 10 marked 1 through 7, two *Spiroplasma*-specific Hsp60 probes revealed presence of amplified gene products in TSE brain tissues but not in normal brain tissues or a water control. FIG. 1 shows presence of 130 and 140 bp amplified PCR products in TSE-infected brains and not in controls. Of the lanes 10, the lane marked 1 shows 100 bp markers. The lanes marked 2 and 5 show water controls. The lanes marked 3 and 6 show normal brain and the lanes marked 4 and 7 show TSE-infected brain. The amplified PCR products are the contrasting bands in the lanes marked 4 and 7. Other non-specific banding represents primer/dimer.

Figure 2:
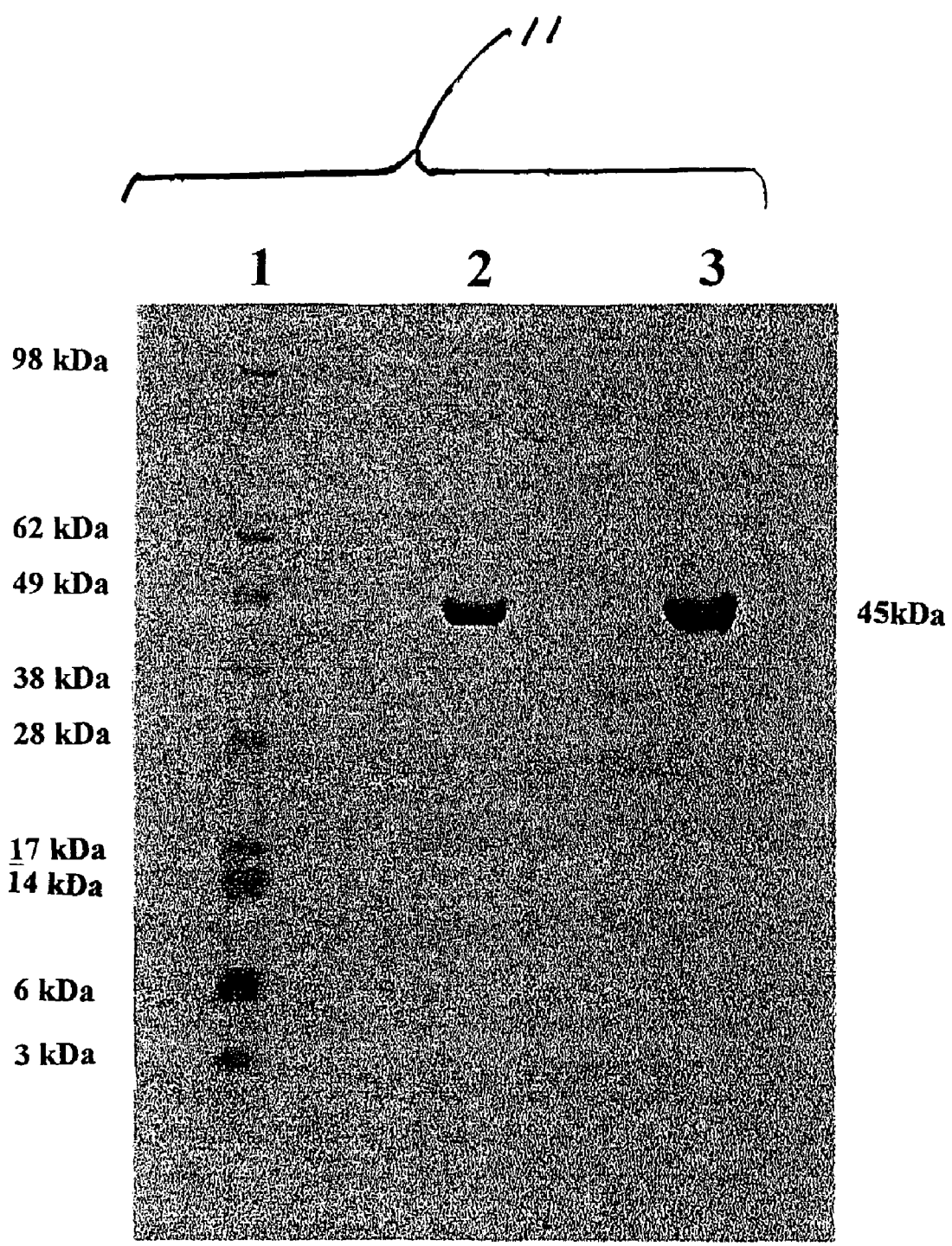
FIG. 2 is an illustrative acrylamide electrophoresis of purified recombinant *Spiroplasma* Hsp60 protein. The 45 kDa GST-tagged recombinant *Spiroplasma* Hsp60 protein eluted from the glutathione column is soluble and in sufficiently pure form (lane 2) for development of an indirect ELISA.

The nucleic acid sequence encoding *Spiroplasma mirum* Hsp60 was placed into a suitable bacterial expression system using GST fusion technology (Novagen). Lysates of bacteria expressing GST bound Hsp60 were used to isolate recombinant Hsp60 of *Spiroplasma mirum* purified by passing through a glutathione column. The recombinant Hsp60 was eluted from the column as a soluble fraction. FIG. 2, which has lanes 11 marked 1, 2 and 3, shows purified soluble fractions of recombinant Hsp60 of 45 kDa size. FIG. 2 shows elution fractions of GST-bound *Spiroplasma* Hsp60 in lanes 11 marked 2 and 3 following passage over a glutathione column. The lane marked 1 shows markers, and the lanes marked 2 and 3, show soluble 45 kDa recombinant *Spiroplasma* Hsp60 protein.

Purified *Spiroplasma mirum* recombinant Hsp60 was attached to the surface of microwell plates. The wells of the plates were blocked with a commercially available blocking buffer. Serum samples from individual patients who were Creutzfeldt-Jakob Disease positive or controls were added to the wells containing the Hsp60 protein. Following an incubation period, the serum samples were removed and each well was washed three times with either tris buffered saline or phosphate buffered saline. A goat anti-human antibody tagged with horseradish peroxidase was added to the wells. Following an incubation period, the wells were washed. A calorimetric substrate was added to the wells. In the presence of horseradish peroxidase, the substrate is oxidized to produce a colored substrate. The amount of analyte produced can be determined by measuring the absorbance of individual samples or wells at the wavelengths produced by the oxidized substrates. All studies were done in triplicate along with three wells with no primary antibody for determining background. An alternate approach would be to use a chemiluminescent substrate of horseradish peroxidase. In such a case, the amount of an analyte can be measured by the relative light units produced.

Figure 3:
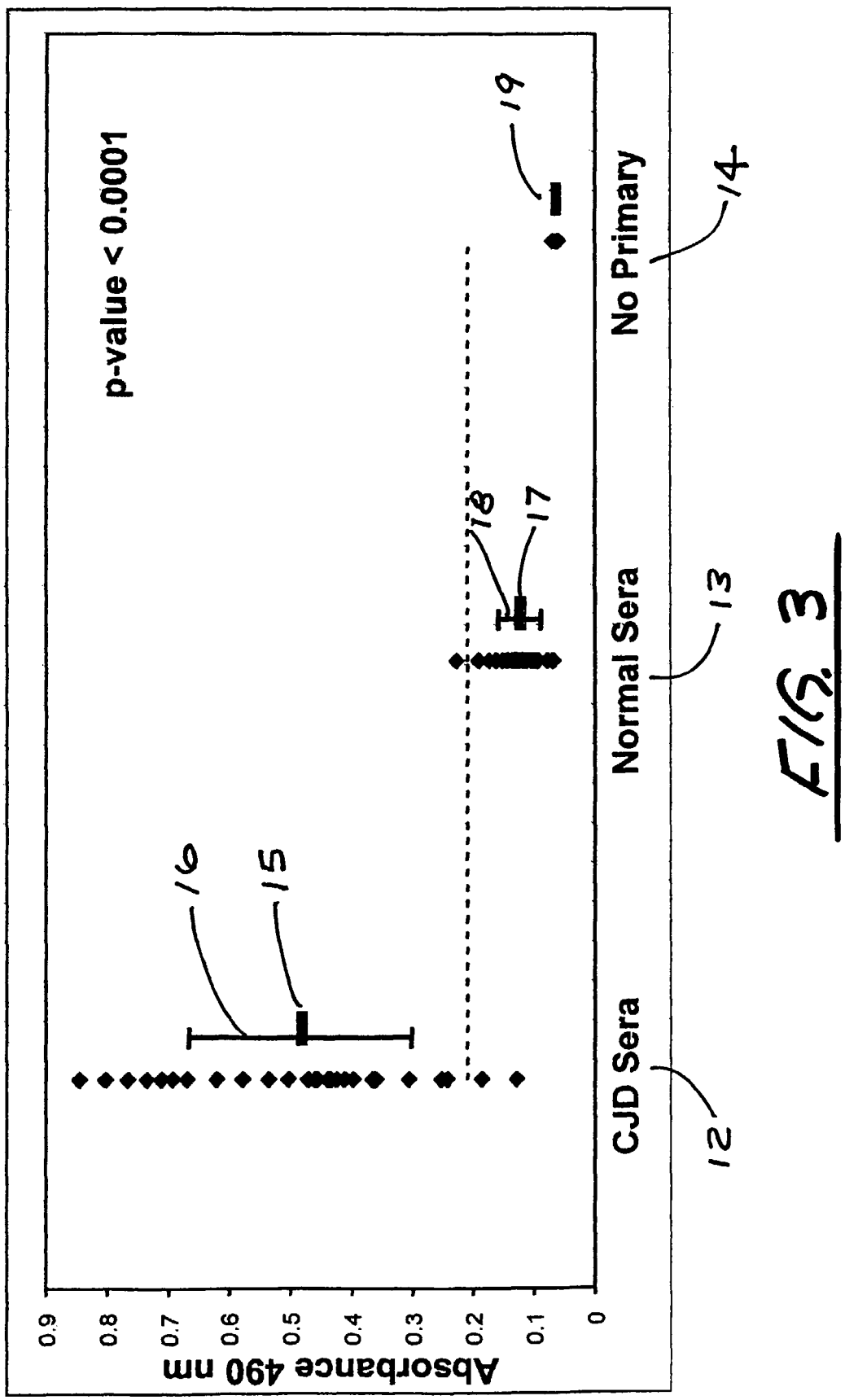
FIG. 3 is a statistical analysis variance table (absorbance at 490 nm of the indirect ELISA plates) showing significant evidence of circulating antibodies against *Spiroplasma* recombinant Hsp60 protein (p-value<0.0001) in sera from CJD patients.

Statistical analysis variance tables (absorbance at 490 nm of the indirect ELISA plates) showed significant evidence of circulating antibodies against *Spiroplasma* recombinant Hsp60 protein (p-value<0.0001) in sera from CJD patients. FIG. 3 compares absorbance readings at 490 nm of thirty individual CJD sera samples compared to thirty individual normal sera. Column 12 shows distribution of plate readings at 490 nm of thirty individual CJD sera showing mean 15 and standard error range 16. Column 13 shows distribution of plate readings at 490 nm of thirty individual normal human sera showing mean 17 and standard error range 18. Column 14 shows plate readings 19 at 490 nm of plate background (no primary antibody).

Figure 4:
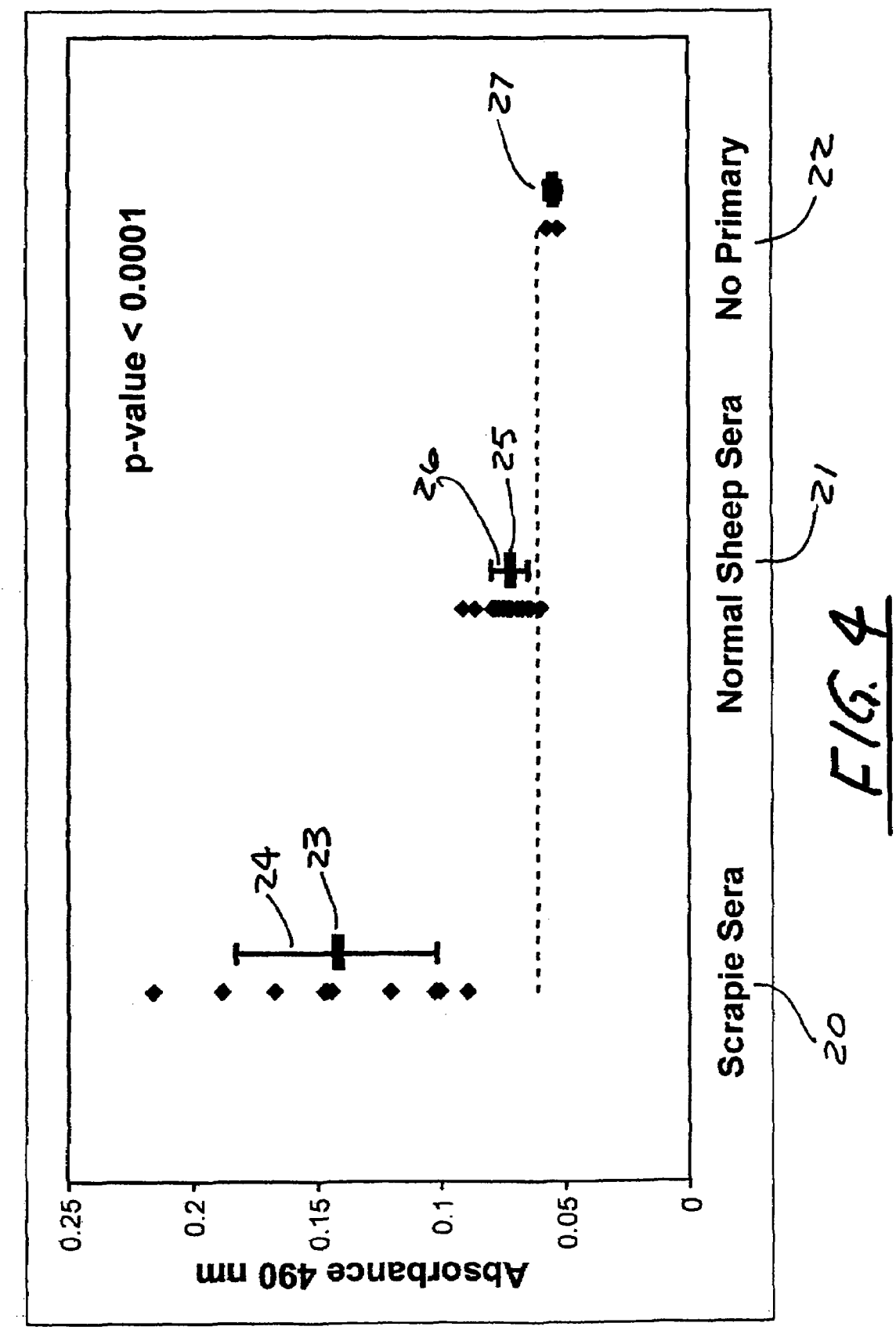
FIG. 4 is a statistical analysis variance table (absorbance at 490 nm of the indirect ELISA plates) showing significant evidence of circulating antibodies against *Spiroplasma* recombinant Hsp60 protein (p-value<0.0001) in sera from scrapie-infected sheep.

Statistical analysis variance tables (absorbance at 490 nm of the indirect ELISA plates) showed significant evidence of circulating antibodies against *Spiroplasma* recombinant Hsp60 protein (p-value<0.0001) in sera from scrapie-infected sheep. FIG. 4 compares absorbance readings at 490 nm of ten individual scrapie sheep sera samples compared to forty individual normal sheep sera. Column 20 shows distribution of plate readings at 490 nm of ten individual scrapie sera showing mean 23 and standard error range 24. Column 21 shows distribution of plate readings at 490 nm of forty individual normal sheep sera showing mean 25 and standard error range 26. Column 22 shows plate readings 27 at 490 nm of plate background (no primary antibody).

The statistical analyses of the ELISA results from the study of thirty individual CJD sera show that there is a >95% confidence in identifying an individual CJD case and a >95% confidence in identifying an individual normal control. Similarly, the study of individual scrapie sera show a >95% confidence in identifying an individual scrapie-infected animal and a >95% confidence in identifying an individual normal control animal.

The invention claimed is:

1. A method of detecting a transmissible spongiform encephalopathy (TSE) disease in a mammal comprising detecting the presence of an antibody to heat shock protein 60 (Hsp60) from a bacterium of the genus *Spiroplasma* in a body fluid sample from the mammal.

2. A method as in claim 1, comprising contacting a serum or plasma sample from a mammal with Hsp60 protein or an antigenic portion of Hsp60 protein from a *Spiroplasma* bacterium and detecting a reaction product of Hsp60 or an antigenic portion thereof with an antibody from the sample.

3. A method as in claim 1, wherein the sample comprises a serum or plasma sample from the mammal.

4. A method as in claim 3, comprising the sequential steps of (a) providing *Spiroplasma* Hsp60 protein or an antigenic portion of Hsp60 protein, bound to a solid substrate to form a diagnostic substrate;

(b) contacting the diagnostic substrate with serum or plasma from a mammal to bind to the diagnostic substrate a primary antibody specific for Hsp60 present in the serum or plasma;

(c) washing the diagnostic substrate to substantially remove proteins from the serum or plasma that are not bound to the diagnostic substrate;

(d) contacting the diagnostic substrate with a secondary antibody specific for the primary antibody of the mammal but not specific for Hsp60 protein to bind the secondary antibody to at least a portion of any primary antibody bound to the diagnostic substrate;

(e) washing the diagnostic substrate to substantially remove non-bound secondary antibody; and (f) measuring the amount of secondary antibody bound to the diagnostic substrate relative to a standard.

5. A method according to claim 1 wherein the mammal is a human.

6. A method according to claim 2 wherein the mammal is a human.

7. A method according to claim 3 wherein the mammal is a human.

8. A method according to claim 4 wherein the mammal is a human.

9. A method according to claim 1 wherein the mammal is a cow.

10. A method according to claim 2 wherein the mammal is a cow.

11. A method according to claim 3 wherein the mammal is a cow.

12. A method according to claim 4 wherein the mammal is a cow.

13. A method according to claim 1 wherein the mammal is a sheep.

14. A method according to claim 2 wherein the mammal is a sheep.

15. A method according to claim 3 wherein the mammal is a sheep.

16. A method according to claim 4 wherein the mammal is a sheep.

17. A method as in claim 1, wherein the sample comprises a cerebrospinal fluid sample from the mammal.

18. A method as in claim 17, comprising contacting a cerebrospinal fluid sample from a mammal with *Spiroplasma* Hsp60 protein or an antigenic portion of Hsp60 protein, and detecting a reaction product of Hsp60 or an antigenic portion thereof with an antibody from the sample.

19. A method as in claim 18, comprising the sequential steps of (a) providing *Spiroplasma* Hsp60 protein or an antigenic portion of Hsp60 protein, bound to a solid substrate to form a diagnostic substrate;

(b) contacting the diagnostic substrate with cerebrospinal fluid from a mammal to bind to the diagnostic substrate a primary antibody specific for Hsp60 present in the cerebrospinal fluid;

(c) washing the diagnostic substrate to substantially remove proteins from the cerebrospinal fluid that are not bound to the diagnostic substrate;

(d) contacting the diagnostic substrate with a secondary antibody specific for the primary antibody of the mammal but not specific for Hsp60 protein to bind the secondary antibody to at least a portion of any primary antibody bound to the diagnostic substrate;

(e) washing the diagnostic substrate to substantially remove non-bound secondary antibody; and (f) measuring the amount of secondary antibody bound to the diagnostic substrate relative to a standard.

20. A method according to claim 17 wherein the mammal is a human.

21. A method according to claim 18 wherein the mammal is a human.

22. A method according to claim 19 wherein the mammal is a human.

23. A method according to claim 17 wherein the mammal is a cow.

24. A method according to claim 18 wherein the mammal is a cow.

25. A method according to claim 19 wherein the mammal is a cow.

26. A method according to claim 17 wherein the mammal is a sheep.

27. A method according to claim 18 wherein the mammal is a sheep.

28. A method according to claim 19 wherein the mammal is a sheep.

29. An isolated Hsp60 protein having the amino acid residue sequence of SEQ ID NO: 2.

30. An isolated polynucleotide encoding an Hsp60 protein having the amino acid residue sequence of SEQ ID NO: 2.

31. An isolated polynucleotide having the nucleotide sequence of SEQ ID NO: 1.

* * * * *